US008293966B2

(12) United States Patent
Obele

(10) Patent No.: US 8,293,966 B2
(45) Date of Patent: Oct. 23, 2012

(54) FEMININE HYGIENE PAD

(76) Inventor: Paralee Obele, Sedona, AZ (US)

( * ) Notice: Subject to any disclaimer, the term of this patent is extended or adjusted under 35 U.S.C. 154(b) by 1132 days.

(21) Appl. No.: 11/679,389

(22) Filed: Feb. 27, 2007

(65) Prior Publication Data

US 2007/0287972 A1 Dec. 13, 2007

Related U.S. Application Data

(60) Provisional application No. 60/812,181, filed on Jun. 9, 2006.

(51) Int. Cl.
*A61F 13/15* (2006.01)

(52) U.S. Cl. .......................................... 604/361

(58) Field of Classification Search .................. 604/361, 604/385.02, 385.201
See application file for complete search history.

(56) References Cited

U.S. PATENT DOCUMENTS

| 4,589,876 A * | 5/1986 | Van Tilburg ............. 604/385.04 |
| 2003/0114811 A1* | 6/2003 | Christon et al. .............. 604/362 |
| 2006/0058770 A1* | 3/2006 | Bohlen et al. .......... 604/385.201 |

* cited by examiner

*Primary Examiner* — Melanie Hand
(74) *Attorney, Agent, or Firm* — Zeman-Mullen & Ford, LLP

(57) ABSTRACT

A feminine hygiene pad having at least a top and bottom layer comprised of the same varying solid colors which match the color of undergarments and/or outerwear of a user to further mask the existence of the pad. The top layer of the feminine hygiene pad may also include a small center area devoid of color in order to detect saturation.

11 Claims, 5 Drawing Sheets

FEMININE HYGIENE PAD

CROSS-REFERENCE TO RELATED APPLICATIONS

This application claims priority to provisional patent application having Ser. No. 60/812,181, filed Jun. 9, 2006, which is herein incorporated in its entirety.

FIELD OF INVENTION

The present invention is generally directed to a feminine hygiene pad, and more particularly, to a feminine hygiene pad comprised of varying solid colors which match the color of undergarments and/or outerwear of a user to further mask the existence of the pad. The feminine hygiene pad may also be comprised of varying colors with a small center area devoid of color in order to detect saturation.

BACKGROUND OF THE INVENTION

A great number of feminine hygiene pads have been developed and designed to place in the crotch area of women's undergarments to capture menstrual flow. Many of the existing pads differ in shape, size, dimension, and thickness. In addition, despite these varying characteristics of feminine hygiene pads, the pads can still be noticeable and visible through outerwear especially when the outerwear is thin, transparent, or light in color.

Accordingly, there is a need for an improved feminine hygiene pad which further functions to mask and hide the appearance of the pad.

SUMMARY OF THE INVENTION

The present invention is directed to a feminine hygiene pad which may be comprised of any shape, thickness, texture, dimension, or size. The pad is entirely comprised of various solid colors, and textures if desired, so that the pad matches or blends with the clothing to which the pad is secured. The color of the pad may be configured to match the color of the undergarment and/or the outerwear of a user. The texture, material or fabric of the pad may also be configured to match the texture, material, or fabric of the undergarment of a user.

The feminine hygiene pad of the present invention includes a top absorbing layer and a bottom fluid-resistant layer where the top and bottom layers comprise the same color or color pattern. The top absorbing layer may also comprise a material layer that matches the fabric or texture of a user's undergarment. In addition, an adhesive is attached to at least a portion of the bottom of the bottom layer to secure the feminine hygiene pad to the undergarment or garment of a user. The top absorbent layer may or may not have at least one tab with adhesive extending from its outer circumference to further secure the pad to the undergarment or garment of a user. The tab would also comprise the same color as the top and bottom layers. In addition, the top layer may comprise a material layer secured thereto which matches the fabric or texture of a user's undergarment and this material layer, like the tab, would also comprise the same color as the top and bottom layers. The pad may also include at least one additional middle absorbent layer that is either 1) the same color or color pattern as the top and bottom layers or 2) secured between the top and bottom layers so that it is not visible.

In another exemplary embodiment of the invention, the feminine hygiene pad of the present invention includes a top absorbing layer and a bottom fluid-resistant layer where the top and bottom layers comprise the same color or color pattern with the exception of a small area or portion at the center of the top absorbing layer. The small area at the center of the top absorbing layer comprises a light color that enables one to detect initial saturation of the pad. The top absorbing layer of the feminine hygiene pad in this embodiment may also comprise a material layer comprising the same fabric or texture as the undergarment of a user. The feminine hygiene pad of the present invention does not show through undergarments and garments and instead blends in with the color of the undergarments and/or outer garments that the user is wearing.

It will also be understood by those skilled in the art that the present invention is equally applicable to the strings of feminine tampons. The strings attached to feminine tampons, all of which are currently white, may also be configured to match the color or colors of a user's undergarment and/or outerwear.

BRIEF DESCRIPTION OF THE DRAWINGS

The present invention is hereafter described in conjunction with the following drawing figures, wherein like numerals demote like elements, and.

DETAILED DESCRIPTION

Figure 1:
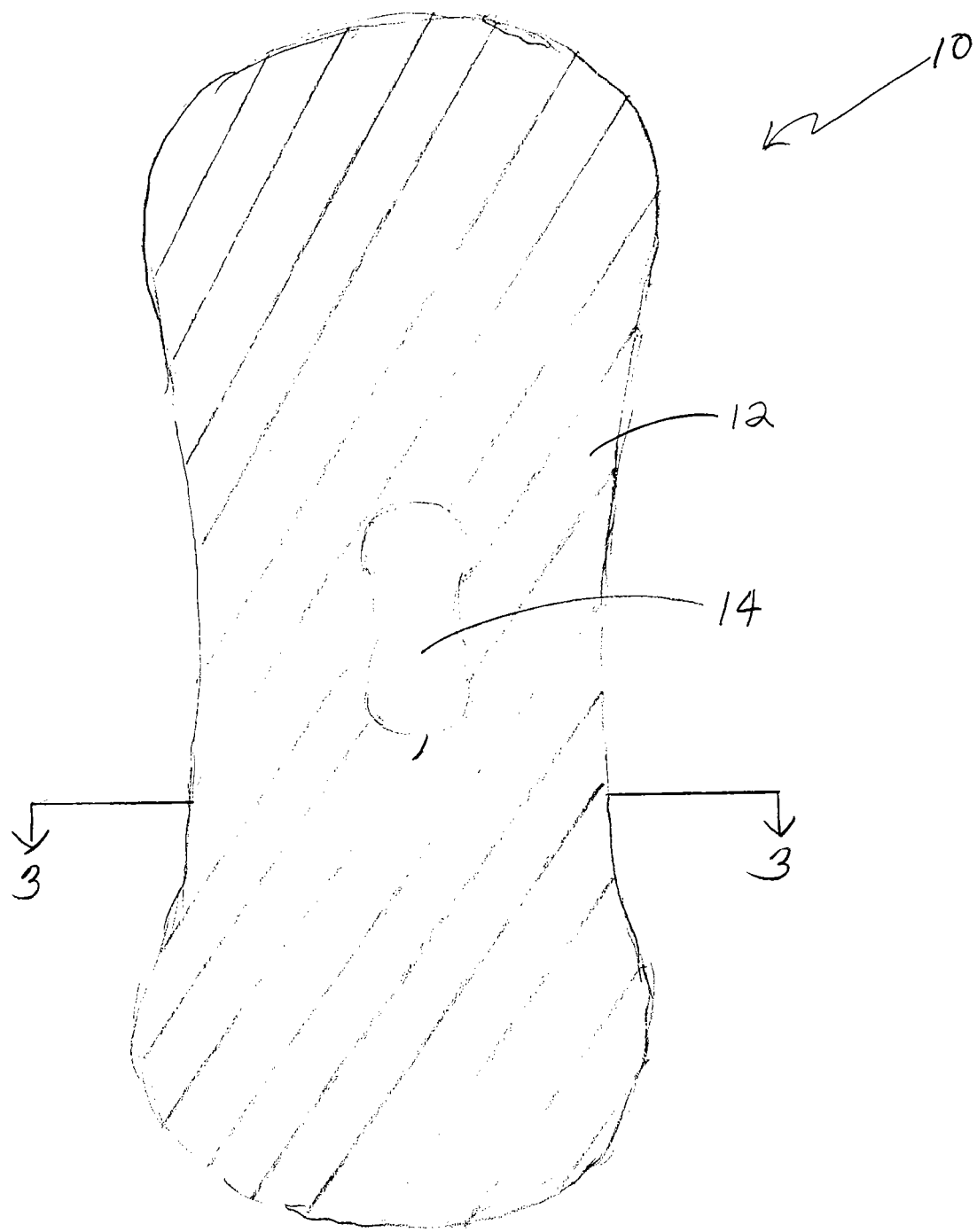
FIG. 1 is a top plan view of one exemplary embodiment of a feminine hygiene pad in accordance with the present invention where the hatched area represents a solid color.

The present invention is generally directed to a feminine hygiene pad that is configured to blend in with the undergarments and/or outerwear of a user. FIG. 1 shows a top plan view of one exemplary embodiment of a feminine hygiene pad in accordance with the present invention where the hatched area represents a solid color. The feminine hygiene pad 10 includes a top absorbing layer 12 having a small area 14 located near or around the center of the top absorbing layer 12. The solid color represented by hatch marks is meant to depict a color that matches to a user's undergarments and/or outerwear. It will also be understood by those skilled in the art that top absorbing layer 12 may comprise a color pattern as well as a solid color. In addition, top absorbing layer 12 may also include a material layer 13 attached thereto which matches the texture or fabric of the undergarment of a user. For example, the material layer 13 may comprise a number of fabrics, including but not limited to, a lace fabric, a cotton fabric, or a silk fabric. Small area 14 of top absorbing layer 12 is sufficiently light in color to visibly detect initial saturation of top absorbing layer 12. Feminine hygiene pad 10 also includes a bottom fluid-resistant (i.e. non-absorbing) layer 16 (See FIG. 2) attached to the top absorbing layer 12. Bottom fluid-resistant layer 16 is the same color as top absorbing layer 12 and is configured to match a user's undergarment or outerwear.

Examples of solid colors which may be used for top absorbing layer 12 and bottom fluid-resistant layer 16 include, but are not limited to, nude, tan, beige, pink, brown, navy, and black. Other popular colors chosen for undergarments as well as a wide range of colors chosen for outerwear may also be used including, but not limited to, orange, red, yellow, blue, green and purple. It will be understood by those in the art that any color or color pattern can be used for the feminine hygiene pad of the present invention. Top absorbing layer 12 may also comprise any number of absorbent textures, materials, or fabrics, without the addition of material layer 13, that may simulate the texture or fabric of a user's undergarment. Feminine hygiene pad 10 also includes an adhesive layer 18 (See FIGS. 3 and 4) attached to the bottom of the bottom fluid-resistant layer 16 for securing the feminine hygiene pad 10 to a user's undergarment or garment. The adhesive layer 18 is preferably transparent and may cover all or just a portion or portions of the bottom of bottom fluid-resistant layer 16.

Figure 3:
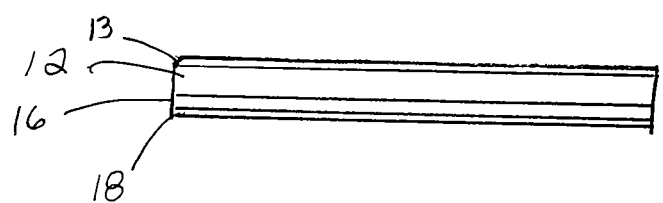
FIG. 3 is a cross-section taken along line 3-3 of FIG. 1.
Figure 4:
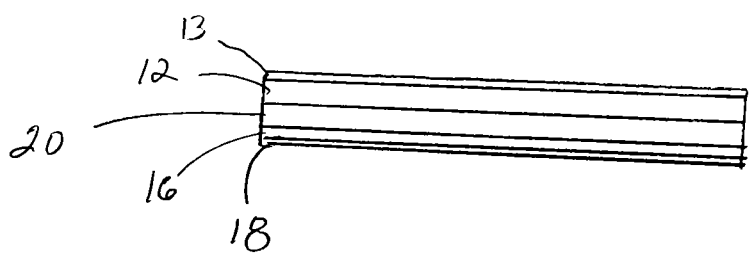
FIG. 4 is another-cross section of the feminine hygiene pad of the present invention showing an additional absorbent layer.

Turning now to FIG. 3, a cross-section taken along line 3-3 of FIG. 1 is shown. FIG. 3 shows an adhesive layer 18 attached to bottom non-absorbent layer 16 which is attached to top absorbing layer 12. FIG. 4 shows a cross section of another exemplary embodiment of the feminine hygiene pad of the present invention. The embodiment show in FIG. 4 is the same as that shown in FIG. 3 with the exception of an addition middle absorbing layer 20 added between the top absorbing layer 12 and the bottom non-absorbent layer 16. In will be understood by those skilled in the art that one or more middle absorbing layers may be added between top absorbing layer 12 and bottom non-absorbent layer 16 as long as any middle absorbing layers are either the same color as the top absorbing layer 12 and bottom non-absorbent layer 16, or secured between the top and bottom layers 12 and 16 so that they are not visible.

Figure 5:
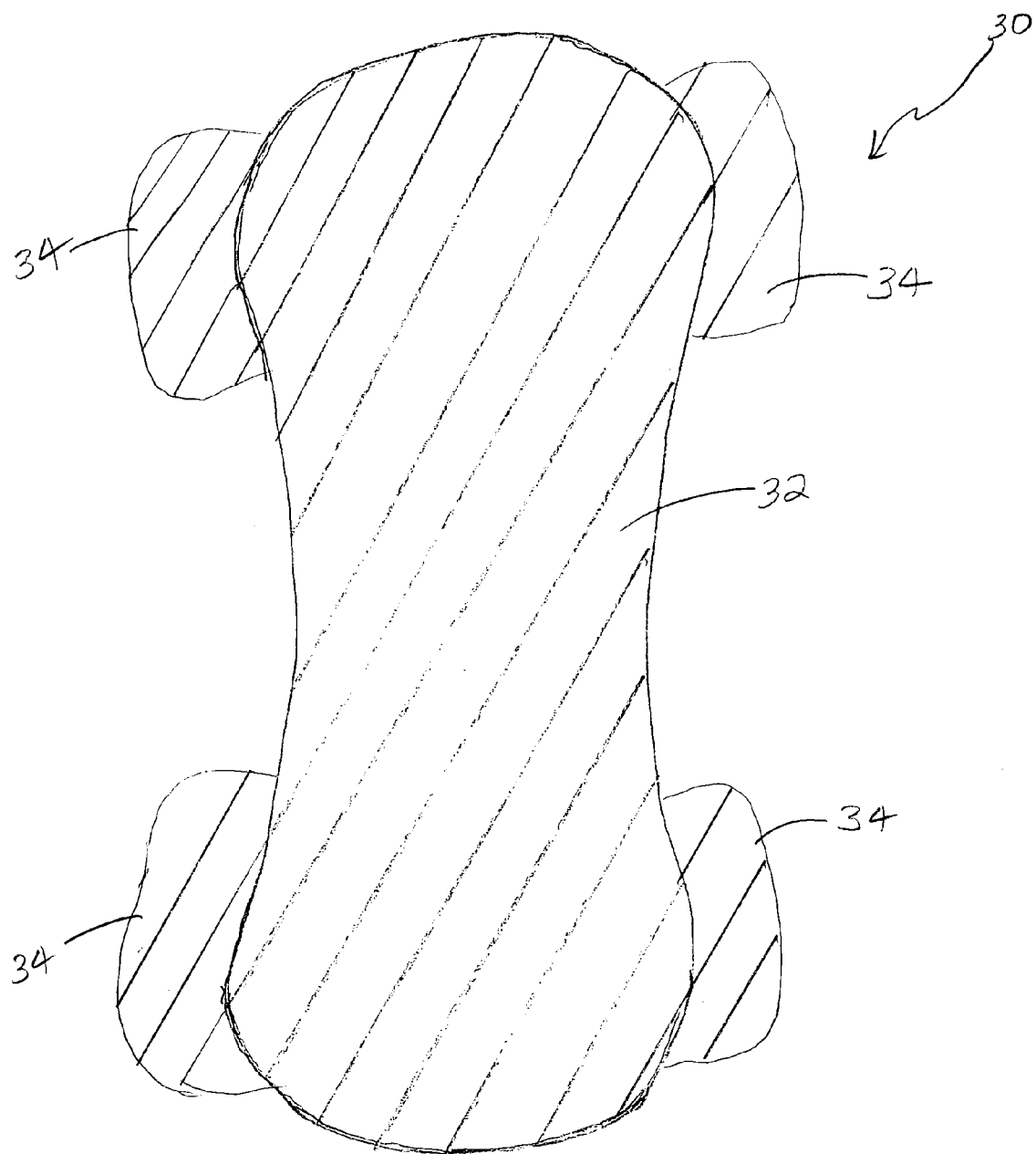
FIG. 5 is a top plan view of another exemplary embodiment of a feminine hygiene pad in accordance with the present invention.
Figure 6:
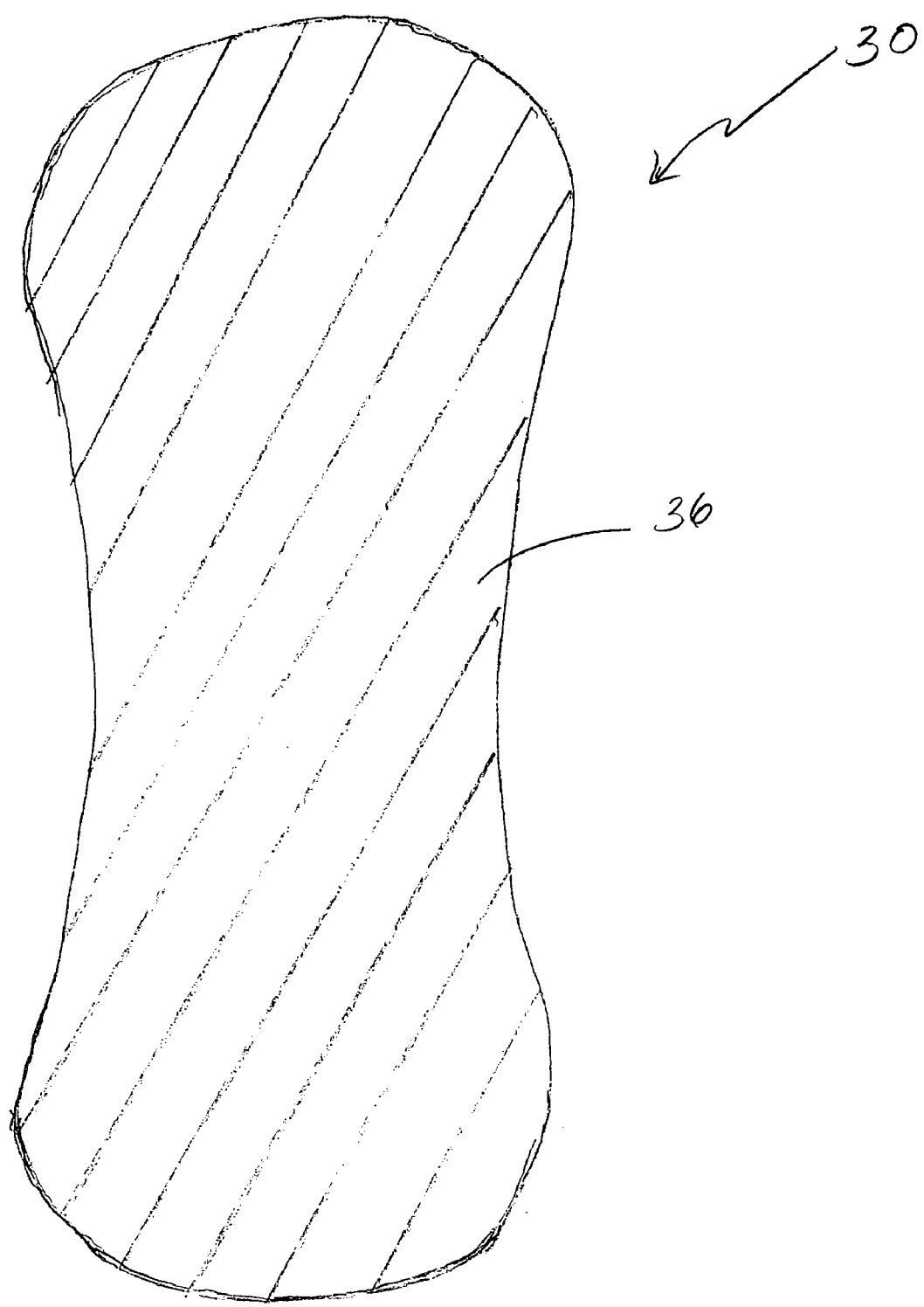
FIG. 6 is a bottom plan view of the feminine hygiene pad shown in FIG. 5.

FIG. 5 is a top plan view of another exemplary embodiment of a feminine hygiene pad in accordance with the present invention and FIG. 6 is a bottom plan view of the same. Feminine hygiene pad 30 includes a top absorbing layer 32 that comprises a non-white solid color or color pattern. Top absorbing layer 32 may include tab members 34 which are comprised of the same non-white color or color pattern of top absorbing layer 32. Tab member 34 may also comprise the same type of texture, material, or fabric as top absorbing layer 32. Tab members 34 include an adhesive, preferably transparent, on at least one portion of a bottom of each of tab members 34 for securing tab members 34 to a bottom non-absorbent layer 36 (See FIG. 6) of feminine hygiene pad 30 after folding tab members 34 around the outside perimeter of top absorbing layer 32 and bottom non-absorbent layer 36. Bottom non-absorbent layer 36 is shown in FIG. 6 and also comprises the same non-white color or color-pattern as top absorbing layer 32. Examples of solid colors which may be used for top absorbing layer 12 and bottom fluid-resistant layer 16 include, but are not limited to, nude, tan, beige, pink, brown, navy, and black. Other popular colors chosen for undergarments as well as a wide range of colors chosen for outerwear may also be used including, but not limited to, orange, red, yellow, blue, green and purple. It will be understood by those in the art that any color or color pattern can be used for the feminine hygiene pad of the present invention.

Figure 2:
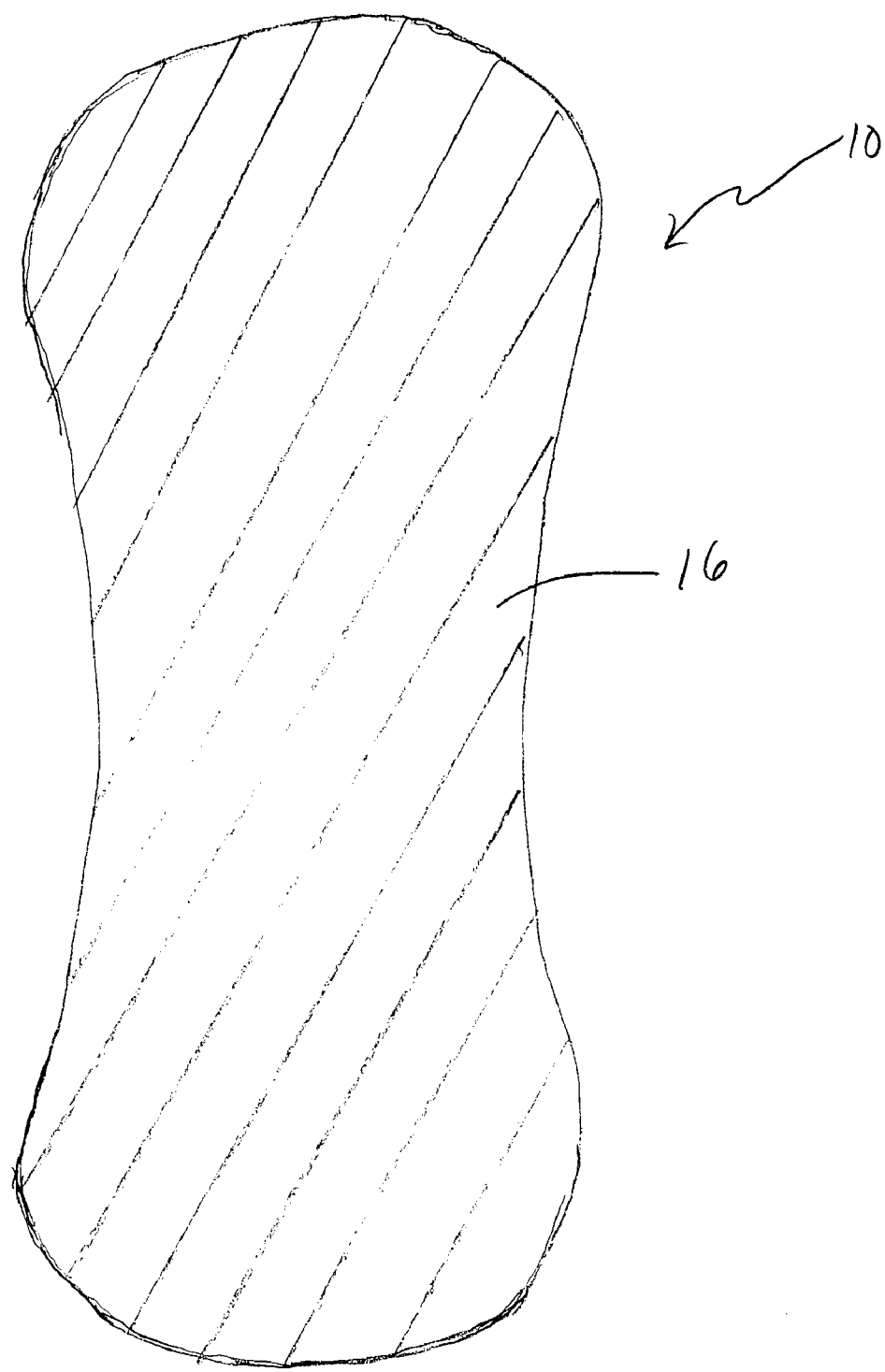
FIG. 2 is a bottom plan view of the feminine hygiene pad in shown in FIG. 1 where the hatched area represents a solid color.

Like the exemplary embodiment shown in FIGS. 1 and 2, one or more middle absorbing layers may also be included in the exemplary embodiment shown in FIGS. 5 and 6. The one or more middle absorbing layers may be added between top absorbing layer 12 and bottom non-absorbent layer 16 as long as any middle absorbing layers are either the same color as the top absorbing layer 12 and bottom non-absorbent layer 16, or secured between the top and bottom layers 12 and 16 so that they are not visible.

The top absorbing layer and any middle absorbing layers of the exemplary embodiments of the feminine hygiene pads of the present invention may be made of any material that provides sufficient absorption to give the pad utility for its intended use. Typical materials include, but are not limited to tissue, woven fabrics, fibers, and micro fibers. In addition, a layer of material comprising the same color as the top absorbing layer and the bottom non-absorbent layer and the same texture or fabric of a user's undergarment may cover the top absorbing layer. Likewise, the bottom non-absorbent layer of the exemplary embodiments of the feminine hygiene pad of the present invention may also be made of any material that provides sufficient impermeability to give the pad utility for its intended use. Typical materials include, but are not limited to, polypropylenes and polyethylenes.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A feminine hygiene pad comprising:
   a bottom non-absorbent layer having a predetermined color;
   a top absorbing layer comprising the same color as the bottom layer with the exception of a small area located near or around a center of the top absorbing layer that is lighter in color than both the bottom and top layers so that a user can detect initial saturation of the top absorbing layer by viewing the small area; and
   an adhesive secured to at least a portion of the bottom non-absorbent layer for retaining the pad in place in an undergarment or garment.

2. The pad of claim 1 wherein the color of the top and bottom layers are dark and a color of the small area of the top layer is light.

3. The pad of claim 2 wherein the color of the top and bottom layers is black.

4. The pad of claim 1 wherein the small area of the top layer is reinforced with additional absorbent material.

5. The pad of claim 1 further comprising at least one middle absorbent layer located between the top and bottom layers.

6. The pad of claim 1 wherein the adhesive is transparent.

7. The pad of claim 1 further comprising at least one tab member having an adhesive thereon for further securing the pad to an undergarment or garment.

8. The pad of claim 7 wherein the adhesive is transparent.

9. The pad of claim 1 wherein the top and bottom layers comprise a same pattern of color.

10. The pad of claim 1 further comprising a material layer having a same color as the top absorbing layer and the bottom non-absorbent layer secured to a top of the top absorbing layer.

11. The pad of claim 10 wherein the material layer matches at least one of a fabric or texture of a user's undergarment.

* * * * *